United States Patent [19]

Clark et al.

[11] Patent Number: 4,794,774
[45] Date of Patent: Jan. 3, 1989

[54] METHOD OF PREPARING A DENTAL RESTORATION

[75] Inventors: Danny R. Clark, Weatherford, Tex.; Asami Tanaka, Skokie, Ill.

[73] Assignee: Tanaka Dental Enterprises, Skokie, Ill.

[21] Appl. No.: 79,475

[22] Filed: Jul. 29, 1987

[51] Int. Cl.⁴ .............................................. B21D 22/10
[52] U.S. Cl. ............................................. 72/63; 72/60; 264/19
[58] Field of Search ....................... 72/60, 63; 264/19

[56] References Cited

U.S. PATENT DOCUMENTS

| | | |
|---|---|---|
| 7,272 | 8/1876 | McDermut . |
| 605,223 | 6/1898 | Gartrell .................................. 72/63 |
| 669,279 | 3/1901 | Harrington ............................. 72/63 |
| 757,938 | 4/1904 | Lyon ....................................... 72/63 |
| 2,887,717 | 5/1959 | Smith . |
| 3,607,996 | 9/1971 | Pickands . |
| 4,182,238 | 1/1980 | Mitchell, Sr. et al. . |
| 4,395,219 | 7/1983 | Franken et al. . |
| 4,459,112 | 7/1984 | Shoher et al. . |
| 4,562,882 | 1/1986 | Alleluia . |
| 4,582,682 | 4/1986 | Betz et al. . |
| 4,585,417 | 4/1986 | Sozio et al. . |
| 4,588,368 | 5/1986 | Buhler et al. . |
| 4,691,857 | 9/1987 | Friedman .............................. 72/63 |

OTHER PUBLICATIONS

Day et al., "Flexobond A Direct Adaptation Technique for Metal Substrates," Trends and Tech. in the Contem. Dental Lab., v. 3, No. 7, pp. 21-26, Sept. 1986.
The Renaissance Crown: "Update on Strength and Versatility," Trends and Tech. in the Contem. Dental Lab., v. 3, No. 7, pp. 49-50, Sep. 1986.

Primary Examiner—W. Donald Bray
Attorney, Agent, or Firm—Neuman, Williams, Anderson & Olson

[57] ABSTRACT

A method is provided for uniformly fitting a foil to a die in the manufacture of a porcelain-metal dental restoration, the method including the application isostatic pressure to a foil covered die. The inventive method is more economical and not as laborious as prior art methods, and provides a superior fit of the foil to the die, resulting in a better quality restoration.

9 Claims, 1 Drawing Sheet

METHOD OF PREPARING A DENTAL RESTORATION

This invention relates to a method of preparing a dental restoration comprising porcelain baked on a metal foil. More particularly, this invention relates to a method of preparing a dental restoration comprising porcelain baked on a metal foil and including an improved method of shaping the foil prior to application of the porcelain thereto.

BACKGROUND OF THE INVENTION

Artificial dental restorations are typically made of one or more layers of dental porcelain applied to a metal substrate. Typically the porcelain is applied to a cast metal base. The cast metal base is relatively thick and is made by casting the molten metal using the well known lost wax technique. Dental porcelain is applied to the cast metal base and the entire structure is baked at high a temperature. The thickness of the cast metal base is typically 0.3 to 0.5 mm. This thickness can be disadvantageous because it minimizes the permissible thickness of the translucent porcelain. In addition, the success of the restoration depends to a great extent on the skill of the practitioner in preparing the cast metal base.

An alternative dental restoration involves forming a crown of dental porcelain on a foil made of a noble metal such as platinum. (An improved metal foil for metal-porcelain dental restorations of this type is disclosed in co-pending application Ser. No. 049,119 filed May 13, 1987.) Generally, these foils can have a thickness of 200 microns or less. The thin platinum foil is shaped to a replica, or die, of the prepared tooth and the dental porcelain is then overlaid onto the foil which supports the porcelain during the subsequent firing cycles. It has been noted that this procedure is extremely technique-sensitive, requiring skillful and meticulous processing. As observed in U.S. Pat. No. 4,585,417 issued Apr. 29, 1986 to Sozia et al., proper and accurate shaping of the platinum foil over the replica is extremely difficult, and these difficulties frequently lead to poorly fitted crowns.

Various techniques have been proposed for fitting metal foils over a die of a prepared tooth. These techniques typically include some sort of swaging step to get as close a fit as possible between the foil and the die. Thus, U.S. Pat. No. 4,459,112 issued July 10, 1984 to Shoher et al. discloses a method of forming a crown wherein a circular foil is placed over a die and carefully folded into at least three pleats. The pleats are folded in an overlapping formation, and either the foil is swaged or pressure is applied by hand. Another technique as set forth in Trends & Techniques in the Contemporary Dental Laboratory, Vol. 3, No. 7, September, 1986, pp. 21-25, involves carefully cutting and folding the foil around the die, then "swedging" the foil covered die by surrounding it with a putty-like material and subjecting that material to hydraulic pressure via hammer blows to a plunger. These prior art methods are laborious and time consuming. Further, they require great skill on the part of the clinician to fit the foil completely uniformly around the die. In addition, standard dental dies are made of gypsum and like materials which can be cracked or otherwise damaged when subjected to swaging procedures. Even if the underlying die is not completely destroyed, sharp edges and other fine details of the die structure can be marred or altered by the swaging process.

SUMMARY OF THE INVENTION

It is thus one object of the invention to provide an improved method of fitting a metal foil to a die for preparation of a dental restoration.

It is another object of the invention to provide such an improved method of fitting a metal foil to a die that is less laborious and time consuming than methods of the prior art.

It is another object of the invention to provide such an improved method of fitting a metal foil to a die that provides greater uniformity of the fit of the foil to the die.

It is still another object of the invention to provide an improved method of fitting a metal foil to a die that does not risk damage to or alteration of the shape of the underlying die.

Other objects, advantages, and novel features of the invention will be readily apparent to one skilled in the art upon reading the following disclosure, including the drawings and claims.

In accordance with the invention, a method is provided for fitting a metal foil to a die for preparation of a dental restoration by means of the application of isostatic pressure to the foil covered die. Foil is applied to the die by standard folding and crimping methods. The foil covered die is placed in a fluid-impermeable but flexible sack, the sack is sealed, and the sack is placed in an isostatic press device. Isostatic pressure is applied to the sack and thus to the foil covered die, thereby uniformly pressing the foil to the die. The isostatic pressure can be in the range of 1000-2500 psi. The method is quick, simple, inexpensive, and provides uniform results. Many individual sacks, each containing a foil covered die, can be placed in the isostatic press device and subjected to isostatic pressure at the same time, thus making the method even more cost effective. Because the pressure is applied isostatically, the method does not create any risk of damage to the underlying die, or alteration of any of the features of the die.

DETAILED DESCRIPTION OF THE INVENTION

For convenience, the following detailed description of the method of the instant invention is made with reference to a particular hydraulic isostatic press device which has been found suitable for carrying out the invention. Those skilled in the art will recognize that other hydraulic isostatic press devices having like features can be used.

Figure 1:
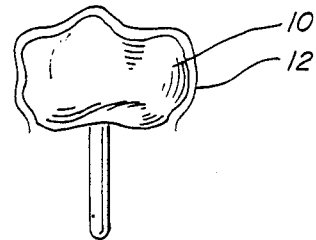
FIG. 1 shows a piece of metal foil applied to a die in anticipation of preparation of a dental restoration.

As shown in FIG. 1, a die 10 of a prepared tooth requiring a dental restoration is fitted with a metal foil 12. The metal foil 12 may be initially fitted to the die 10 by standard folding and crimping techniques. Before the application of pressure to the foil covered die, the fit of the foil to the die will not be uniform within the close tolerances required for a high quality metal porcelain dental restoration.

Figure 2:
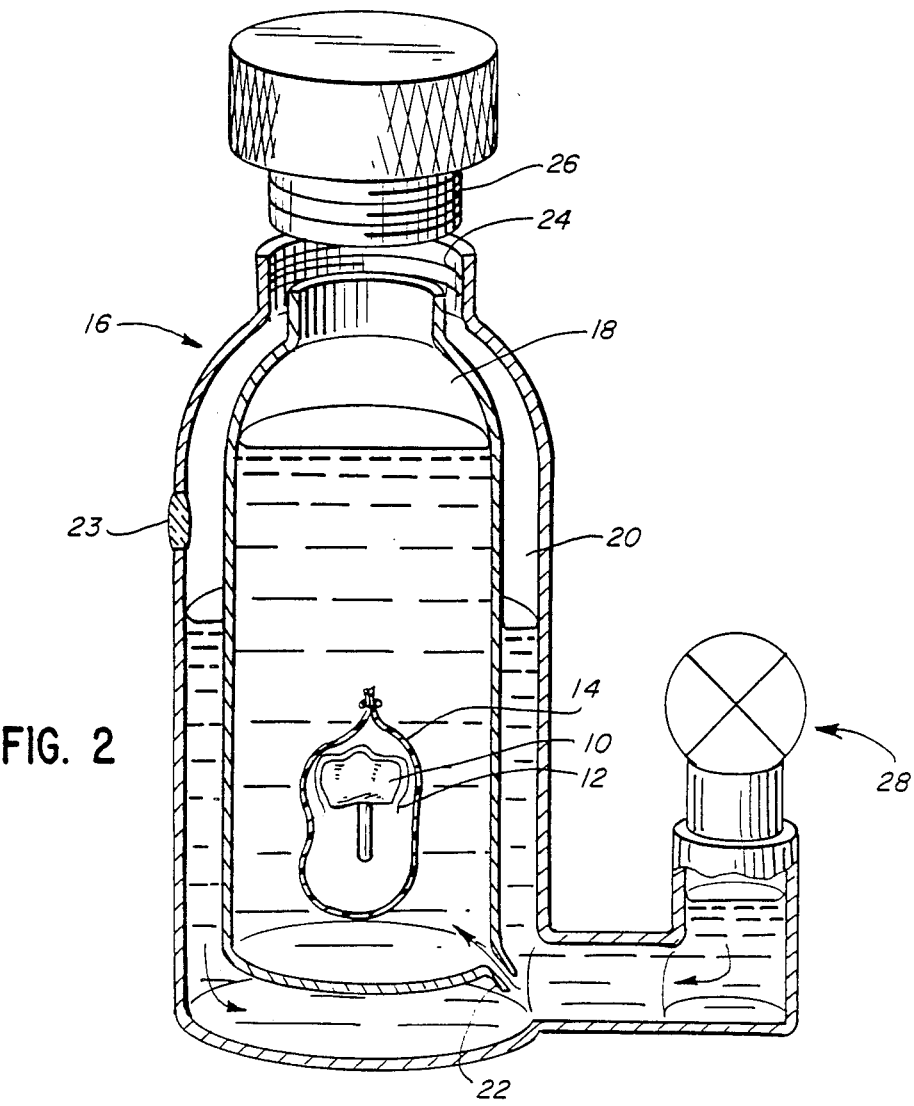
FIG. 2 is a schematic diagram of one type of isostatic press device suitable for use with the method of the instant invention.

The foil-covered die is then placed in a flexible, fluid impermeable sack 14 and the sack is sealed. Thin, highly elastic rubber is a suitable material for this purpose. An isostatic press device 16 such as shown schematically in FIG. 2 is provided, and the sack 14 containing the foil covered die is placed in the main chamber 18 thereof. The chamber 18 is double walled such that annular envelope 20 surrounds chamber 18. Annular envelope 20 and chamber 18 are in fluid communication by means of port 22. Fluid is introduced into chamber 18 and also enters annular envelope 20 through port 22. A viewing port 23 is provided in the outer wall of annular envelope 20 to allow the operator to check the level of the fluid therein.

Isostatic press 16 is further provided with a threaded neck portion 24 and a mating threaded cap 26. Pump 28 is in fluid communication with annular envelope 20. Pump 28 may be of any commonly known type such as a simple and inexpensive hand pump. After the sack 14 containing foil covered die 10 is placed in chamber 18, said chamber 18 is filled with fluid, which may be water, ethylene glycol, oil, or any other fluid typically used in isostatic presses. Threaded cap 26 is fitted part way down into threaded neck portion 24, and pressure is applied to the system by means of pump 28 to bleed out excess air until a small amount of fluid is expelled from neck portion 24. When that occurs, the operator knows that all excess air has been removed. Cap 26 is then fitted the rest of the way down into neck portion 24 to seal the system. The operator then applies further pressure to the system via pump 28. It may be seen that this results in the application of pressure such that the fluid transmits the pressure isostatically through sack 14 to uniformly press foil 12 against die 10. The isostatic pressure may be in the range of 1000 to 2500 psi. When completed, the pressure is released from the system, sack 14 is removed from chamber 18 and foil covered die 10 is removed from sack 14.

The foregoing inventive method provides a superior uniform fit of foil 12 to die 10. This superior, uniform fit is accomplished quickly and easily, and is not as technique-sensitive as methods of the prior art. Furthermore, it may be seen that the method of the instant invention allows several foil covered dies to be prepared at one time, because chamber 18 can accommodate more than one sack 14 at a time. The method of the instant invention greatly improves the speed and economy with which foil-porcelain restorations can be made, and greatly improves the quality of the completed restoration. Furthermore, the success of the method is not dependent on the composition of the foil or on the shape or type of die used.

The technique of the instant invention can also be used to form molds of dies using heat reformable materials. In prior art techniques, wax molds are made by simply applying wax to a die, pressing the wax in place by hand, and removing the die. This procedure does not always produce a good fit between the wax and the die, and also creates internal stresses in the wax due to the nonuniformity of the externally applied pressure. By the technique of the instant invention a mold can be made by covering the die with wax or a plastic that becomes reformable at slightly elevated temperatures, placing the covered die in a fluid-impermeable flexible sack, placing the sack in the aforementioned main chamber of an isostatic press, filling the chamber with an appropriate fluid, applying pressure to the fluid whereby the fluid will exert isostatic pressure on the covered die, and heating the fluid to promote moldability of the wax or plastic around the die. The addition of an appropriate heating element to the apparatus shown in FIG. 2 will be understood by one of ordinary skill in the art. If the fluid used is an oil, then it may be heated to about 70° C. if the mold is to be made of wax, or about 100° C. if the mold is to be made of a low melting plastic material. If wax is used the pressure applied can be 10-30 psi, while higher pressures can be applied if a low melting plastic is used. It will be appreciated that the use of this technique minimizes the internal stresses that would otherwise be present in the mold, thereby giving the mold greater mechanical and thermal stability. It will also be appreciated that the use of the inventive technique provides a much more accurate mold of the die than prior art techniques.

The foregoing description of a preferred embodiment is not intended to limit the scope of the present invention. Other embodiments will be readily apparent to those skilled in the art upon reading the specification and claims and reviewing the drawings.

I claim:

1. A method of preparing an improved metal porcelain dental restoration comprising
   preparing a die of the tooth on which the restoratioin will be fitted,
   covering the die with a metal foil,
   subjecting the foil covered die to isostatic pressure to uniformly press the foil onto the die,
   applying dental porcelain to the pressed foil on the die, and
   baking the porcelain on the foil to fuse the porcelain onto the foil.

2. The method of claim 1 wherein the step of subjecting the foil covered die to hydraulic isostatic pressure includes the steps of placing the foil covered die in a flexible, fluid impermeable sack; placing the sack in an isostatic press which is filled with a fluid; and placing the fluid under isostatic pressure, whereby the pressure is transmitted isostatically from the fluid through the sack to the foil covered die to uniformly press the foil against the die.

3. The method of claim 2 wherein said pressure is in the range of 1000-2500 psi.

4. A method of fitting a foil against a die for purposes of preparing a dental restoration comprising
   providing an isostatic press,
   covering said die with said foil,
   placing said foil covered die in a flexible fluid impermeable sack,
   placing said sack in said isostatic press, and
   applying isostatic pressure on said sack, whereby said isostatic pressure is transmitted through said sack to isostatically press the foil against the die to obtain a superior fit of the foil to the die.

5. The method of claim 4 wherein said pressure is in the range of 1000-2500 psi.

6. A method of preparing a mold of a die comprising
   providing an isostatic press having a chamber containing fluid;
   covering said die with a heat reformable material;
   placing said covered die in a flexible fluid-impermeable sack;
   placing said sack in said chamber of said isostatic press;
   applying pressure to said fluid; and
   applying heat to said fluid, whereby said heat and pressure are transmitted through said sack to said heat reformable material to isostatically press said material against said die to make a mold thereof.

7. The method of claim 6 wherein said heat reformable material is wax and said fluid is heated at about 70° C.

8. The method of claim 7 wherein said applied pressure is about 10–30 psi.

9. The method of claim 6 wherein said heat reformable material is a low melting plastic and said fluid is heated to about 100° C.

* * * * *